United States Patent [19]

Elliott et al.

[11] Patent Number: 4,769,496

[45] Date of Patent: Sep. 6, 1988

[54] SYNTHESIS OF KETONES FROM ALDEHYDES

[75] Inventors: David J. Elliott; Filippo Pennella, both of Bartlesville, Okla.

[73] Assignee: Phillips Petroleum Company, Bartlesville, Okla.

[21] Appl. No.: 62,006

[22] Filed: Jun. 12, 1987

[51] Int. Cl.$^4$ .............................................. C07C 45/49
[52] U.S. Cl. .................................... 568/387; 568/388
[58] Field of Search ................................ 568/387, 388

[56] References Cited

U.S. PATENT DOCUMENTS 4,694,108 9/1987 Elliott ................................. 568/381

Primary Examiner—James H. Reamer
Attorney, Agent, or Firm—K. K. Brandes

[57] ABSTRACT

A process for producing higher ketones comprises the step of contacting under suitable conditions a feed comprising at least one $C_2$–$C_6$ aliphatic aldehyde, and preferably also carbon monoxide, with a catalyst composition comprising (i) copper and/or an oxide thereof and (ii) zinc oxide. Preferably, the feed aldehyde is propanal, and the product comprises at least one $C_5$ ketone. Ketones are substantially absent from the aldehyde feed.

28 Claims, No Drawings

4,769,496

SYNTHESIS OF KETONES FROM ALDEHYDES

BACKGROUND OF THE INVENTION

This invention relates to a catalytic process for preparing ketones. In another aspect, this invention relates to the conversion of aldehydes to higher ketones.

Catalytic processes for converting aldehydes, alone or in admixture with lower ketones, to higher ketones are known. However, there is an ever present need to develop new processes employing different catalysts and/or different coreactants so as to attain more desirable product distributions or higher yields of ketones.

SUMMARY OF THE INVENTION

It is an object of this invention to catalytically convert aldehydes to higher ketones. It is another object of this invention to convert a feed stream comprising an aldehyde and carbon monoxide to higher ketones. It is a further object of this invention to convert propionaldehyde (propanal) to at least one ketone having at least 5 carbon atoms per molecule. Other objects and advantages will be apparent from the detailed description and the appended claims.

In accordance with this invention, a feed comprising at least one aliphatic aldehyde having from 2 to 6 carbon atoms per molecule (preferably propanal) is contacted with a catalyst composition comprising (i) at least one of copper and copper oxide and (ii) zinc oxide, in the substantial absence of ketones (especially ketones having 3–6 carbon atoms per molecule), more preferably also in the substantial absence of alcohols, water, free oxygen and free hydrogen in the feed, under such contacting conditions as to obtain a product comprising at least one higher ketone having at least one carbon atom per molecule more than the aldehyde in said feed. Preferably said higher ketone has at least 5 carbon atoms per molecule, and more preferably is a hexanone.

In a preferred embodiment, the aldehyde-containing feed additionally comprises carbon monoxide. In another preferred embodiment, the feed consists essentially of said at least one aldehyde and carbon monoxide.

In still another preferred embodiment, the catalyst composition in the process of this invention comprises (i) at least one of copper and copper oxide, (ii) zinc oxide and (iii) an inorganic refractory oxide material (more preferably alumina). In a further preferred embodiment, the catalyst composition comprising CuO and ZnO is pretreated by heating with a reducing gas, before the catalyst composition is used in the process of this invention. In a still further preferred embodiment the catalyst composition consists essentially of components (i), (ii) and (iii) as defined above.

DETAILED DESCRIPTION OF THE INVENTION

The catalyst composition employed in the process of this invention comprises (i) oxide of copper and/or copper metal and (ii) zinc oxide. Preferably the mixed oxide of Cu and Zn is prepared by coprecipitation of either the hydroxides of copper and zinc and/or the carbonates of copper and zinc, e.g. by addition of a base such as NaOH, or a soluble carbonate such as $Na_2CO_3$, to an aqueous solution of copper and zinc salts such as nitrates, halides or sulfates of copper and zinc, and subsequent calcination (heating in air) under such conditions as to form the oxides of copper and zinc.

In a preferred embodiment, an inorganic refractory oxide material such as alumina, silica, aluminosilicate (e.g., clay), titania, zirconia, magnesia, aluminum phosphate, zirconium phosphate, mixtures of the above and the like, preferably alumina, is also present in said catalyst composition. More preferably the catalyst composition is prepared by either coprecipitation of hydroxides and/or carbonates of copper, zinc and aluminum and subsequent calcination under such conditions as to form the oxides of copper, zinc and aluminum; or by coprecipitation of hydroxides and/or carbonates of copper and zinc from an aqueous solution containing dispersed alumina, and subsequent calcination; or by the method described in U.S. Pat. No. 3,790,505, herein incorporated by reference. CuO/ZnO containing catalyst compositions are commercially available from United Catalysts, Inc., Louisville, Ky. and from BASF Wyandotte Corporation, Parsippany, N.J.

In a preferred embodiment, a CuO-ZnO containing catalyst composition used in the process of this invention is pretreated by heating with a reducing gas (e.g., $H_2$, and/or CO), preferably a free hydrogen containing gas, so as to partially reduce CuO to $Cu_2O$ and/or Cu metal, before the catalyst composition is employed in the process of this invention. More preferably, said heating is carried out with a free hydrogen containing gas, most preferably a $H_2/N_2$ mixture containing 2–5 volume-% $H_2$, at about 350°–450° F. for about 1–6 hours.

Preferably the weight ratio of Cu (present as metal or oxide) to Zn (present as oxide) in the catalyst composition ranges from about 1:20 to about 20:1, more preferably from about 1:3 to about 3:1. If alumina ($Al_2O_3$) or (less preferably) another inert refractory material as defined above is also present in said catalyst composition, the weight percentage of said inert material (preferably alumina) in the catalyst composition can range from about 1 to about 90 weight-%, preferably from about 10 to about 70 weight-%. Generally the surface area (determined by the BET/$N_2$ method, ASTM D3037) of the catalyst composition ranges from about 10 $m^2/g$ to about 300 $m^2/g$, preferably from about 20 $m^2/g$ to about 200 $m^2/g$.

The feed that is contacted with the CuO-ZnO containing catalyst composition comprises at least one aliphatic aldehyde having from 2 to 6 carbon atoms per molecule. An inert gas such as nitrogen or helium can also be present in said feed stream. The use of hydrogen gas, of oxygen gas, of alcohols and of water as components of the feed is not preferred in the process of this invention. Non-limiting examples of feed aldehydes are acetaldehyde, propanal (propionaldehyde), n-butanal, straight-chain pentanals, $\beta$-substituted pentanals, straight-chain hexanals, $\beta$-substituted hexanals, and mixtures thereof, preferably propanal (propionaldehyde).

In a particularly preferred embodiment, the feed also contains carbon monoxide. The presence of CO in the feed results in higher conversion of the aldehyde and in enhanced selectivity to higher ketones in the formed product. Preferably, the mole ratio of aldehyde to carbon monoxide generally is in the range of from about 1:100 to about 20:1, preferably from about 1:20 to about 1:1.

The aldehyde containing feed can be contacted with the catalyst composition in any suitable manner. A feed stream containing a vaporized aldehyde having from 2 to 6 carbons per molecule, and preferably also a carbon monoxide containing feed stream, can be passed into a suitable reaction vessel, and can then be contacted in at least partially mixed form with the catalyst composition under suitable reaction conditions. The aldehyde containing feed stream can be introduced as a substantially liquid stream, which will then vaporize in the reactor, or it can be introduced as a substantially vaporized stream. When a CO containing feed stream is also used, the two feed streams (as defined above) can be premixed and then be contacted with the catalyst composition under suitable reaction conditions so as to produce a reaction product comprising at least one ketone containing at least one carbon atom per molecule more than the feed aldehyde.

The process of this invention can be carried out as a batch process or as a continuous process. In a batch process, the process ingredients are charged in any order to a vessel equipped with pressuring and heating means, and the ingredients are then kept in contact with the catalyst composition for a certain length of time under suitable reaction conditions so as to produce a product comprising at least one ketone containing at least one C atom per molecule more than the aldehyde. In this type of operation, the catalyst can be dispersed in the feed stream (generally gaseous) as a fluidized bed; or the feed stream can be circulated through a fixed bed containing the catalyst composition. In a continuous process, which is presently preferred, the feed stream(s) can be passed through a fixed bed containing the solid catalyst composition, under such conditions as will result in a product comprising at least one ketone containing at least one C atom per molecule more than the feed aldehyde. Optionally, an inert gas can be present during the batch or continuous process.

Heating of the process ingredients is generally required to accomplish at least partial conversion of the feed aldehyde to at least one ketone containing at least one additional carbon atom per molecule than the aldehyde. Any suitable temperature that will cause and maintain a controllable reaction can be employed. Any feasible heating means can be utilized. It is within the scope of this invention to preheat one or more of the process ingredients before they are introduced into a reactor, which is heated to maintain a suitable temperature. The reaction temperature generally ranges from about 200° C. to about 400° C., preferably from about 250° C. to about 300° C.

The reaction pressure generally is above atmospheric pressure. The selection of the reaction pressure will greatly depend on the reaction temperature, the feed rates of feed and the specific reactor design. Generally, the pressure ranges from about 1 psig to about 5,000 psig, preferably about 200 psig to about 2,000 psig.

The reaction time, i.e., the time of intimate, simultaneous contact of all process ingredients, can vary from 0.01 to about 60 minutes and will preferably be in the range of about 0.1 to about 10 minutes. The actual reaction time will greatly depend on the flow rates of feed aldehyde and, optionally (preferably) carbon monoxide, on the selection of an effective, yet safe reaction temperature, on the extent of mixing and agitation (if any) during the reaction, and on the amount of the catalyst employed. In a continuous process, the gas hourly space velocity of the combined feed stream comprising aldehyde and, optionally, CO ranges generally from about 100 to about 10,000 cc feed stream/cc catalyst/hour, preferably from about 1,000 to about 5,000 cc/cc/hr, measured at about 550° F. and 15 psia.

The formed reaction product which comprises at least one ketone containing at least one C atom per molecule more than the feed aldehyde can be separated from the reaction mixture by any suitable separation means such as condensation, crystallization, absorption, fractional distillation, or extraction with a suitable solvent plus subsequent evaporation of the solvent. Unreacted process ingredients can be at least partially separated in a similar manner and can be recycled to the reaction zone where the conversion of aldehydes to higher ketones occurs in accordance with this invention.

If a reaction product contains more than one ketone and by-products, said product can be separated into the pure components by any of the above-cited or other known separation means. Compositions of products formed from the preferred aldehyde, propanal, under specific reaction conditions are presented in the Examples. Ketones prepared by the process of this invention can be used as solvents and/or as reactants in various organic synthesis.

The following examples are presented to further illustrate this invention without unduly limiting the scope of the invention.

EXAMPLE I

This example illustrates the conversion of propanal to higher ketones, in the presence of a 16/40 mesh CuO-ZnO-Al$_2$O$_3$ catalyst which was prepared substantially in accordance with the procedure of Example I of U.S. Pat. No. 3,790,505, herein incorporated by reference. The catalyst contained about 30 weight-% CuO, about 31 weight-% ZnO and about 39 weight-% Al$_2$O$_3$, and had a BET/N$_2$ surface area of about 42 m$^2$/g. The reactor used was a vertical, tubular, stainless steel reactor having an inner diameter of about one-half inch and a catalyst bed length of about 5–6 inches, and was heated by means of an outside furnace. The reactor was filled as follows: top layer of 5 cc 16 mesh Alundum alumina (having a surface area of less than 1 m$^2$/g; marketed by Norton Chemical Process Products, Akron, Ohio); middle layer of 2.5 cc (3.0 g) of the CuO-ZnO-Al$_2$O$_3$ catalyst plus 7.5 cc 16 mesh Alundum; bottom layer of 5 cc 16 mesh Alundum. A thermocouple was axially inserted into the catalyst bed.

First, the catalyst bed in the reactor was pretreated with a H$_2$/N$_2$ gas mixture (having H$_2$:N$_2$ volume ratio of 3:97) at about 390°–400° F., for a time period of about 4 hours. Then the reactor was purged with nitrogen, the temperature was raised to 540°–550° F., and the required feed streams were charged to the reactor.

In invention run 1, liquid propanal was charged at a rate of 2.9 cc/hr, and nitrogen gas was charged at a rate of 140 cc/min to the reactor so as to provide a combined gas stream containing about 90 volume-% N$_2$. In control run 2, the feed rate of propanal was 2.3 cc/hr and the feed rate of N$_2$ was substantially the same as in run 1, but additionally liquid methyl ethyl ketone (butanone) was charged at a rate of about 2 cc/hr. In both runs, the feed streams were substantially free of alcohols, water, free oxygen and free hydrogen.

The product stream was cooled by a cold trap having a temperature of about 30° F., so as to condense the less volatile components. The off-gas product stream was analyzed by means of a modified Applied Automation Model 12 gas chromatograph (GC), whereas the liquid product was analyzed by means of a Hewlett-Packard Model 5750 gas chromatograph with a methyl silicone lined capillary column. The various components of the liquid product separated by GC were confirmed by mass spectrometry. Results are summarized in Table I.

TABLE I

|  | Run 1 (Invention) | Run 2 (Control) |
|---|---|---|
| Aldehyde Feed | Propanal | Propanal |
| Ketone Feed | None | Butanone |
| Gas Feed | $N_2$ | $N_2$ |
| % Conversion of Propanal | 93 | 85 |
| Composition of Liquid Product: |  |  |
| Wt-% of 1-Propanol | 4.7 | 1.5 |
| Wt-% of Propanal | 6.3 | 8.0 |
| Wt-% of Propionic Acid | — | 6.0 |
| Wt-% of 2-Butanol | — | 0.5 |
| Wt-% of Butanone | — | 42.9 |
| Wt-% of $C_5$ Alcohols | 0.8 | — |
| Wt-% of $C_5$ Ketones | 11.6 | 1.8 |
| Wt-% of $C_6$ Alcohols | 2.9 | — |
| Wt-% of $C_6$ Aldehydes | 6.2 | 5.5 |
| Wt-% of Propyl Propionate | 36.7 | 16.5 |
| Wt-% of $C_6$ Ketones | 6.9 | 1.1 |
| Wt-% of $C_7$ Ketones | — | 12.1 |
| Wt-% of $C_{7+}$ Alcohols and Esters[1] | 15.3 | 3.1 |
| Wt-% of $C_8$ Ketones | 4.8 | — |
| Wt-% of $C_9$ Ketones | 3.6 | 1.0 |

[1] Not identified; number of C atoms per molecule: 7 or higher.

Data in Table I demonstrate that the absence of butanone in the feed unexpectedly resulted in enhanced conversion of propanal and enhanced yield of ketones, in particular $C_6$, $C_8$ and $C_9$ ketones. The total percentage of ketone products in invention run 1 was 27 weight-% whereas the total weight percentage of ketone products in control run 2 was only 16 weight-%.

Analysis of the gas product formed in run 1 revealed that about 99 volume-% was nitrogen, about 0.5 volume-% was hydrogen, and about 0.3 volume-% was carbon dioxide.

EXAMPLE II

This example illustrates the conversion of propanal to higher ketones in the presence of carbon monoxide as co-feed (instead of nitrogen as described in Example I). The feed rate of CO in runs 3 and 4 was 140 cc/minute. The experimental procedure was essentially the same as that described for runs 1 and 2 in Example I, except that CO was used in lieu of $N_2$. Again, alcohols, water, free oxygen and free hydrogen were substantially absent in all feed streams. Pertinent test data are summarized in Table II.

TABLE II

|  | Run 1 (Invention) | Run 3 (Invention) | Run 4 (Control) |
|---|---|---|---|
| Aldehyde Feed | Propanal | Propanal | Propanal |
| Ketone Feed | None | None | Butanone |
| Gas Feed | $N_2$ | CO | CO |
| %-Conversion of Propanal | 93 | 100 | 97 |
| Composition of Liquid Products: |  |  |  |
| Wt-% of 1-Propanol | 4.7 | — | 0.6 |
| Wt-% of Propanal | 6.3 | — | 1.4 |
| Wt-% of Hydrocarbons[1] | — | 3.7[1] | 0.3 |
| Wt-% of $C_4$/$C_5$ Alcohols | 0.8 | — | 1.4 |
| Wt-% of Butanone | — | — | 30.7[5] |
| Wt-% of $C_5$ Ketones | 11.6 | 14.0[2] | 8.2 |
| Wt-% of $C_6$ Alcohols | 2.9 | 3.0 | 0.2 |
| Wt-% of $C_6$ Aldehydes | 6.2 | — | — |
| Wt-% of Propyl Propionate | 36.7 | 5.4 | 9.0 |
| Wt-% of $C_6$ Ketones | 6.9 | 46.5[3] | 10.2 |
| Wt-% of $C_7$ Ketones | — | 4.3 | 23.4 |
| Wt-% of $C_{7+}$ Alcohols and Esters[4] | 15.3 | 8.2 | 0.6 |
| Wt-% of $C_8$ Ketones | 4.8 | 6.4 | 3.6 |
| Wt-% of $C_9$ Ketones | 3.6 | 5.8 | — |

[1] Mainly $C_3$-$C_6$ olefins
[2] Mainly diethyl ketone
[3] Mainly ethyl isopropyl ketone
[4] Not identified
[5] Unreacted feed ketone Data in Table II clearly show that the conversion of propanal and the yield of ketones were increased when CO was present in the aldehyde feed (compare runs 1 and 3). Furthermore, run 3 (without a ketone in the feed) produced more higher ($C_5$-$C_9$) ketones than run 4 (which contained a ketone as a co-feed). The total percentage of $C_5$-$C_9$ product ketones was 77 weight-% in invention run 3 and only about 45 weight-% in control run 4. Thus the absence of lower ketone in the aldehyde feed quite surprisingly caused an increase in selectivity to higher ketones.

Analysis of the gas product formed in run 3 revealed that about 96.3 volume-% was carbon monoxide, about 3.1 volume-% was carbon dioxide, and about 0.5 volume-% was $H_2$.

Reasonable variations and modifications are possible within the scope of the disclosure and the appended claims.

We claim:

1. A process for preparing higher ketones comprising the step of contacting a feed comprising at least one aliphatic aldehyde having from 2 to 6 carbon atoms per molecule with a catalyst composition comprising
  (i) at least one of copper and copper oxide, and
  (ii) zinc oxide,
in the substantial absence of ketones in said feed, under such contacting conditions as to obtain a product comprising at least one ketone having at least one carbon atom per molecule more than said aliphatic aldehyde.

2. A process in accordance with claim 1, wherein free hydrogen, free oxygen, alcohols and water are substantially absent from said feed.

3. A process in accordance with claim 1, wherein said catalyst composition additionally comprises (iii) inorganic refractory oxide support material.

4. A process in accordance with claim 3, wherein catalyst component (iii) is alumina.

5. A process in accordance with claim 1, wherein said aliphatic aldehyde is propanal.

6. A process in accordance with claim 5, wherein said product comprises at least one ketone having at least 5 carbon atoms per molecule.

7. A process in accordance with claim 1, wherein the weight ratio of Cu to Zn in said catalyst composition is in the range of from aobut 1:20 to about 20:1.

8. A process in accordance with claim 7, wherein said weight ratio of Cu to Zn is in the range of from about 1:30 to about 3:1.

9. A process in accordance with claim 1, wherein said catalyst composition additionally comprises alumina and the weight percentage of alumina in said catalyst composition is in the range of from about 1 to about 90 weight-%.

10. A process in accordance with claim 9, wherein said weight percentage of alumina is in the range of from about 10 to about 70 weight-%, and the surface area of said catalyst composition is in the range of from about 10 to about 300 m²/g.

11. A process in accordance with claim 1, wherein said catalyst has been pretreated with a reducing gas under such conditions as to at least partially reduce CuO, which is present in said catalyst composition, to at least one of $Cu_2O$ and Cu.

12. A process in accordance with claim 1, wherein said contacting conditions comprise a reaction temperature in the range of from about 200° to about 400° C., a reaction pressure in the range of from about 1 to about 5,000 psig, and a reaction time in the range of from about 0.01 to about 60 minutes.

13. A process in accordance with claim 12, wherein said reaction temperature is in the range of from about 250° to about 300° C. and said reaction pressure is in the range of from about 200 to about 2000 psig.

14. A process for preparing higher ketones comprising the step of contacting a feed comprising
(a) at least one aliphatic aldehyde having from 2 to 6 carbon atoms per molecule, and
(b) carbon monoxide,
with a catalyst composition comprising
(i) at least one of copper and copper oxide and
(ii) zinc oxide,
in the substantial absence of ketones in said feed, under such contacting conditions as to obtain a product comprising at least one ketone having at least one carbon atom per molecule more than said aliphatic aldehyde.

15. A process in accordance with claim 14, wherein free hydrogen, free oxygen, alcohols and water are substantially absent from said feed.

16. A process in accordance with claim 14, wherein said catalyst composition additionally comprises (iii) inorganic refractory oxide support material.

17. A process in accordance with claim 16, wherein catalyst component (iii) is alumina.

18. A process in accordance with claim 14, wherein said said aliphatic aldehyde is propanal.

19. A process in accordance with claim 18, wherein said product comprises at least one ketone having at least 5 carbon atoms per molecule.

20. A process in accordance with claim 14, wherein the mole ratio of aliphatic aldehyde to carbon monoxide is in the range of from about 1:100 to about 20:1.

21. A process in accordance with claim 20, wherein said mole ratio of aliphatic aldehyde to carbon monoxide is in the range of from about 1:20 to about 1:1.

22. A process in accordance with claim 14, wherein the weight ratio of Cu to Zn in said catalyst composition is in the range of from about 1:20 to about 20:1.

23. A process in accordance with claim 22, wherein said weight ratio of Cu to Zn is in the range of from about 1:30 to about 3:1.

24. A process in accordance with claim 14, wherein said catalyst composition additionally comprises alumina and the weight percentage of alumina in said catalyst composition is in the range of from about 1 to about 90 weight-%.

25. A process in accordance with claim 24, wherein said weight percentage of alumina is in the range of from about 10 to about 70 weight-%, and the surface area of said catalyst composition is in the range of from about 10 to about 300 m²/g.

26. A process in accordance with claim 14, wherein said catalyst has been pretreated with a reducing gas under such conditions as to at least partially reduce CuO, which is present in said catalyst composition, to at least one of $Cu_2O$ and Cu.

27. A process in accordance with claim 14, wherein said contacting conditions comprise a reaction temperature in the range of from about 200° to about 400° C., a reaction pressure in the range of from about 1 to about 5,000 psig, and a reaction time in the range of from about 0.01 to about 60 minutes.

28. A process in accordance with claim 27, wherein said reaction temperature is in the range of from about 250° to about 300° C., and said reaction pressure is in the range of from about 200 to about 2000 psig.

* * * * *